United States Patent [19]
Cannata et al.

[11] Patent Number: 5,808,156
[45] Date of Patent: Sep. 15, 1998

[54] PROCESS FOR THE PRODUCTION OF THE ISOMERS (R) AND (S)-α-METHYL-3 (TRIFLUOROMETHYL) BENZENEETHANAMINE

[75] Inventors: Vincenzo Cannata, Bologna; Barbara Galbiati; Tiziano Ferrario, both of Milan, all of Italy

[73] Assignee: Alfa Chemicals Italiana S.p.A., Bergamo, Italy

[21] Appl. No.: 904,338

[22] Filed: Jul. 31, 1997

[30]     Foreign Application Priority Data

Apr. 29, 1997  [IT]  Italy ............................... BO97 A 0252

[51] Int. Cl.[6] ........................ C07C 209/28; C07C 209/88
[52] U.S. Cl. ............................. 564/381; 564/304
[58] Field of Search ..................... 564/381, 304

[56]       References Cited

U.S. PATENT DOCUMENTS 3,198,833  8/1965  Beregi et al. ........................... 564/381

FOREIGN PATENT DOCUMENTS 1413078  11/1975  United Kingdom .

OTHER PUBLICATIONS

Abstract 74597W/45 of GB 1413–070, Nov. 1975.
Jacewicz, Chemical Abstracts, vol. 84, abstract 30637, 1976.
Jacewicz, Chemical Abstracts, vol. 84, abstract 30636, 1976.

*Primary Examiner*—Richard L. Raymond
*Attorney, Agent, or Firm*—Bucknam and Archer

[57]          ABSTRACT

Process for the production of the isomers (R) and (S)-α-methyl-3-(trifluoromethyl)benzeneethanamine, the second being useful as intermediate in the synthesis of the anorexic drug dexfenfluramine (INN), which comprises carrying out a stereospecific reductive amination of 1-(3-trifluoromethyl) phenyl-2-propanone with (R) or (S)-α-methylbenzylamine under a hydrogen atmosphere in the presence of a catalyst and debenzylating the resulting diastereoisomer (R),(R) or (S),(S)-N-(1-phenylethyl)-α-methyl-3-(trifluoromethyl) benzeneethanamine by treatment with hydrogen and a catalyst.

4 Claims, No Drawings

PROCESS FOR THE PRODUCTION OF THE ISOMERS (R) AND (S)-α-METHYL-3 (TRIFLUOROMETHYL) BENZENEETHANAMINE

BACKGROUND OF THE INVENTION

The dexfenfluramine (INN) is the dextrorotatory isomer of the fenfluramine, well-known anorexic drug described in U.S. Pat. No. 3,198,833.

The separation of the two optical isomers of the fenfluramine, in order to get the dextrorotatory isomer much more active than the levorotatory isomer, has been first described in U.S. Pat. No. 3,198,834.

It is a classic example of optical resolution through the formation of diastereoisomer salts first with the (+)-dibenzoyltartaric acid and then with the (+)-camphoric acid.

The yield of dexfenfluramine is very low, about 11% calculated as the racemate, and the process is very troubled as it requires the crystallization of two different diastereoisomer salts.

Stereospecific syntheses have been tried in order to get only the dexfenfluramine to avoid the low yields and the high costs for the separation of the optical isomers through the crystallization of the diastereoisomer salts with optically active acids.

European Patent 0,301,925 describes the enantiospecific production of the dexfenfluramine by starting from the (S)-2-amino-1-propanol through a series of stereospecific condensations and reductions.

European Patent 0,441,160 in its turn describes the enantiospecific production of the dexfenfluramine starting from (S)-1-(3-trifluoromethyl)phenyl-2-propanol obtained by inversion of the (R)-1-(3-trifluoromethyl)phenyl-2-propanol obtained in its turn by enantioselective enzymatic reduction of the corresponding ketone.

The present invention refers to a process for the production of the isomers (R) and (S)-α-methyl-3-(trifluoromethyl) benzeneethanamine, from the second of which the dexfenfluramine can be obtained through an alkylation reaction. This process provides for a first step comprising a stereospecific reductive amination of 1-(3-trifluoromethyl)phenyl-2-propanone with (R) or (S)-α-methylbenzylamine, intermediates industrially available at accessible prices, under a hydrogen atmosphere in the presence of a catalyst to respectively give the (R),(R) or the (S),(S)-N-(1-phenylethyl)-α-methyl-3-(trifluoromethyl)benzeneethanamine, new compounds, which by treatment with hydrogen and catalyst give the (R) or the (S)-α-methyl-3-(trifluoromethyl) benzeneethanamine.

DESCRIPTION OF THE INVENTION

Process for the production of (R) and of (S)-α-methyl-3-(trifluoromethyl)benzeneethanamine of formula

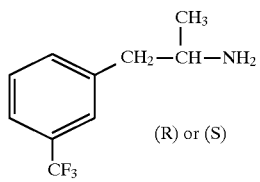

the second of which is useful as intermediate for the production of the dexfenfluramine, which comprises:

a) carrying out a stereospecific reductive amination with (R) or (S)-α-methylbenzylamine of formula

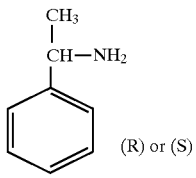

on the 1-(3-trifluoromethyl)phenyl-2-propanone of formula

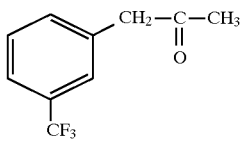

to respectively give the diastereoisomer (R),(R) or (S),(S)-N-(1-phenylethyl)-α-methyl-3-(trifluoromethyl) benzeneethanamine of formula

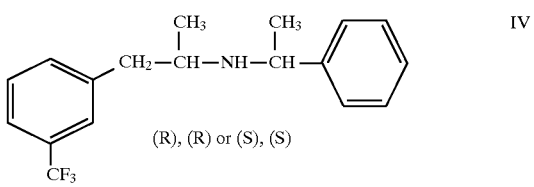

b) carrying out a reductive debenzylation of the compound of formula IV or of a salt thereof with an organic or inorganic salt.

The intermediates of formula IV and the salts thereof with organic or inorganic acids are new compounds and are claimed as such.

The salts particularly preferred in carrying out the invention are the hydrochlorides.

Step a) is carried out by reacting in a hydrogenator from 1 to 3 molar equivalents of (R) or (S)-α-methylbenzylamine and one molar equivalent of 1-(3-trifluoromethyl)phenyl-2-propanone in a polar solvent or mixture of polar and non-polar solvents in the presence of a catalyst and, optionally, of an organic or inorganic acid under from 1 to 20 hydrogen atmospheres at a temperature between 20° C. and 100° C. for a period of time between 2 and 24 hours.

In a preferred aspect of the invention the polar solvent is an alcohol containing from 1 to 6 carbon atoms, the catalyst is Raney nickel and the acid is acetic acid.

At the end of the reaction, the reaction mixture is filtered to eliminate the catalyst and the solvent can be eliminated under vacuum obtaining the crude product of formula IV in the form of an oil.

The reaction product, obtained as a base base form, can be purified by salification with an organic or inorganic acid in a solvent or mixture of polar and non-polar solvents and subsequent crystallization of the organic or inorganic salt. The product of formula IV can be obtained again in the form of a free base by treating the organic or inorganic salt with an alkaline base, for instance with an aqueous solution of sodium hydroxide.

In a preferred aspect of the invention the product is purified by crystallization of the hydrochloride obtained by adding aqueous hydrochloric acid to a mixture of the crude product in a solvent or solvents mixture.

The pure crystalline hydrochloride of the compound of formula IV can, in its turn, give again the pure base of formula IV by treatment with an alkaline base like the sodium hydroxide in aqueous solution.

Step b) is carried out by debenzylating the compound of formula IV or a salt thereof with an organic or inorganic acid in a polar solvent or mixture of polar and non-polar solvents in an hydrogenator in the presence of a catalyst under from 1 to 20 atmospheres of hydrogen at a temperature between 20° and 100° C. for a period of time between 2 and 24 hours.

In a preferred aspect of the invention the polar solvent is an alcohol containing from 1 to 6 carbon atoms and the catalyst is palladium on carbon.

At the end of the reaction the reaction mixture is filtered to eliminate the catalyst and the solvent is eliminated under vacuum obtaining the crude product of formula I.

This product can be alkylated as such or after purification by salification with organic or inorganic acids in order to get the dexfenfluramine.

The $^1$H-NMR and $^{13}$C-NMR spectra have been recorded by means of a Varian's NMR Gemini® spectrometer operating respectively at the 300 and 75.45 Mhz frequencies.

Tetramethylsilane has been taken as starting point ((0 ppm).

The examples hereinbelow reported are a further illustration of the invention and have not to be considered as limitation.

EXAMPLE 1

(S),(S)-N-(1-phenylethyl)-α-methyl-3-(trifluoromethyl) benzeneethanamine hydrochloride A mixture made by 300 ml of methanol, 50 g (0.247 moles) of 1-(3-trifluoromethyl)phenyl-2-propanone, 30 g (0.247 moles) of (S)-α-methylbenzylamine and 4 g of Raney nickel is introduced into a hydrogenator, the temperature of the reaction mixture is raised from 20° C. to 75° C. and the reaction is carried out at this temperature for a period of 8 hours while keeping a constant pressure of hydrogen at 8 atmospheres.

The reaction mixture is then cooled to room temperature, filtered and the resulting solution is evaporated under vacuum in order to eliminate the solvent obtaining a colourless oil. Then the oil is mixed with 80 ml of toluene and 40 ml of water, the mixture is heated to 50° C. and acidified to pH 2 by means of a 37% (w/w) aqueous solution of hydrochloric acid. The mixture is then cooled to 5° C. under strong stirring and the crystalline product is filtered, washed on the filter with 30 ml of water and 40 ml of toluene and dried under vacuum to 60° C. for 6 hours.

55 Grams of (S),(S)-N-(1-phenylethyl)-α-methyl-3-(trifluoromethyl) benzeneethanamine hydrochloride are obtained containing 99% of the (S),(S) isomer and 1% of (R),(S) isomer with a yield equal to 65% calculated over the starting 1-(3-trifluoromethyl)phenyl-2-propanone.

The product has the following chemical-physical characteristics:

$[\alpha]^{25}_D = -14.3°$ (c=2% in ethanol)

m.p.=203°±1° C. $^1$H-NMR (CDCl$_3$) δ1.45 (d, 3H, CH$_3$CH), 1.99 (d, 3H, CH$_3$CHCH$_2$), 3.03 (dd, 1H, CH$_2$), 3.48 (m, 1H, CH$_3$CHCH$_2$), 3.74 (dd, 1H, CH$_2$), 4.94 (q, 1H, CH$_3$CH), 7.63 (m, 2H, Ar), 7.72–7.89 (m, 7H, Ar). $^{13}$C-NMR (CDCl$_3$) δ16.9 (Me), 20.5 (Me), 39.2 (CH$_2$), 54.9 (CH), 57.4 (CH), 125.4 (CH, Ar), 125.8 (quat, CF$_3$), 127.2 (CH, Ar), 129.1 (CH, Ar), 130.99 (CH, Ar), 131.05 (CH, Ar), 131.11 (CH, Ar), 132.4 (quat, Ar, C-CF$_3$), 134.5 (CH, Ar), 138.1 (quat, Ar), 139.3 (quat, Ar).

EXAMPLE 2

(S),(S)-N-(1-phenylethyl)-α-methyl-3-(trifluoromethyl) benzeneethanamine

The product obtained in example 1 is suspended in 250 ml of toluene and added under strong stirring to a 1N aqueous solution of sodium hydroxide until constant pH 11. The two layers are separated after one hour of stirring, the aqueous layer is extracted with 100 ml of toluene and then is discarded. The organic layers are collected, twice washed with 50 ml of water and then the organic solvent is eliminated by evaporation under vacuum.

The so obtained pure (S),(S)-N-(1-phenylethyl)-α-methyl-3-(trifluoromethyl)benzeneethanamine is a colourless oil having the following chemical-physical characteristic:

$[\alpha]^{25}_D = -29.3°$ (c=2% in ethanol)

EXAMPLE 3

(S)-α-methyl-3-(trifluoromethyl)benzeneethanamine

The (S),(S)-N-(1-phenylethyl)-α-methyl-3-(trifluoromethyl)benzeneethanamine obtained in example 2 is dissolved into 150 ml of methanol and then put into a hydrogenator together with 2.5 g of 5% palladium on wet carbon at 50%.

A hydrogen atmosphere is kept into the hydrogenator at the constant pressure of 5 atmospheres at the temperature of 50° C. for a period of time of 4 hours.

The reaction mixture is then filtered and the solvent is evaporated under vacuum. The oily residue is diluted with 70 ml of toluene and 50 ml of water and the mixture is acidified to pH 1 with a 37% (w/w) aqueous solution of hydrochloric acid.

The two layers are separated: the organic layer is discarded while the aqueous layer is twice washed with 15 ml of toluene and then is added to 100 ml of toluene and 50 ml of water and made alkaline to pH 12.5 with a 30% (w/v) aqueous solution of sodium hydroxide.

The layers are separated, the aqueous layer is discarded while the organic layer, after two washings with 20 ml of water, is evaporated under vacuum in order to eliminate the solvent.

27.8 Grams of pure (S)-α-methyl-3-(trifluoromethyl) benzeneethanamine are obtained having a specific rotatory power $[\alpha]^{25}_D = +20.8°$ (c=1% in ethanol) with a yield equal to 92% calculated on the bases of the starting (S),(S)-N-(1-phenylethyl)-α-methyl-3-(trifluoromethyl) benzeneethanamine hydrochloride described in example 1.

EXAMPLE 4

(S)-α-methyl-3-(trifluoromethyl)benzeneethanamine

2 Kilograms (5.819 moles) of (S),(S)-N-(1-phenylethyl)-α-methyl-3-(trifluoromethyl)benzeneethanamine hydrochloride and 44 g of 5% palladium on wet carbon at 50% are put into a hydrogenator together with 6 l of methanol.

A hydrogen atmosphere is kept into the hydrogenator at the constant pressure of 5 atmospheres at the temperature of 75° C. for a period of time of 4 hours. The reaction mixture is then filtered in order to remove the catalyst and the methanol is evaporated off under vacuum obtaining a solid, white, crystalline residue which is dissolved into 2 l of water. The so obtained solution is distilled in order to remove the ethylbenzene and then is made alkaline to pH 12.5 with a 30% (w/w) aqueous solution of sodium hydroxide. The two layers are separated, the aqueous layer is discarded while the organic layer is three times washed with 200 ml of water and then is distilled under vacuum. 1081 Grams of (S)-α-methyl-3-(trifluoromethyl)benzeneethanamine are obtained in the form of a clear colourless oil with a yield equal to 92%.

$[\alpha]^{25}_D = +20.5°$ (c=1% in ethanol)

EXAMPLE 5

(S),(S)-N-(1-phenylethyl)-α-methyl-3-(trifluoromethyl) benzeneethanamine hydrochloride A mixture made of 6 l of methanol, 1000 g (4.95 moles) of 1-(3-trifluoromethyl)phenyl-2-propanone, 600 g (4.95 moles) of (S)-α-methylbenzylamine, 80 g of Raney nickel and 149 g of acetic acid is introduced into a hydrogenator, the temperature of the reaction mixture is raised from 20° C. to 75° C. and the reaction is carried out at this temperature for a period of 20 hours while keeping a constant hydrogen pressure of 8 atmosphere.

The reaction mixture is then cooled to room temperature, filtered and the resulting solution is evaporated under vacuum in order to remove the solvent.

The obtained product is then mixed with 750 ml of water and 1500 ml of toluene and the mixture is brought to pH 10 by means of a 30% (w/w) aqueous solution of sodium hydroxide.

The layers are separated, the aqueous layer is discarded while the organic layer is added to 750 ml of water and the resulting mixture is heated up to 50° C. and brought to pH 2 by means of a 37% (w/w) aqueous solution of hydrochloric acid. The mixture is cooled to 5° C. and the precipitated crystalline solid is filtered, washed first with water and then with toluene and dried under vacuum to 60° C. for 6 hours. 1420 Grams of product are obtained having the following characteristic:

diastereoisomeric ratio: 98% (S),(S) and 2% (R),(S)

$[\alpha]^{25}_D = -15.1°$ (c=2% in ethanol).

The yield is equal to 83.5%.

EXAMPLE 6

(S),(S)-N-(1-phenylethyl)-α-methyl-3-(trifluoromethyl) benzeneethanamine hydrochloride The reaction is carried out with the same amounts of reagents and the same manner as those described in example 5 until the filtration of the reaction mixture. The resulting solution is concentrated to half volume and brought to pH 1.5 by adding a 37% (w/w) aqueous solution of hydrochloric acid.

The temperature of the mixture goes up to 40° C. and 3000 ml of water are added under stirring while keeping the temperature at 40° C. for one hour.

The suspension is then cooled to 5° C., filtered and the crystalline solid is washed with a 50/50 water/methanol mixture and dried under vacuum at 60° C. for 6 hours.

1410 Grams of pure product, containing 99.3% of (S),(S) isomer and 0.7% of (R),(S) isomer are obtained, with a yield equal to 82.8%

$[\alpha]^{25}_D = -14.2°$ (c=2% in ethanol)

m.p.=203°±1° C.

EXAMPLE 7

(R),(R)-N-(1-phenylethyl)-α-methyl-3-(trifluoromethyl) benzeneethanamine hydrochloride By working according to the same amounts and manner as those of example 1, substituting the (S)-α-methylbenzylamine with the (R)-α-methylbenzylamine, the diastereoisomer named in the title is obtained with similar yields, pure, having the following chemical-physical characteristic:

$[\alpha]^{25}_D = +14.1°$ (c=2% in ethanol)

EXAMPLE 8

(R),(R)-N-(1-phenylethyl)-α-methyl-3-(trifluoromethyl) benzeneethanamine

The product described in the title is obtained in the form of colourless oily substance having a specific rotatory power $[\alpha]^{25}_D = +29.4°$ (c=2% in ethanol) from the product from in example 7 by working according to the manner described in example 2.

EXAMPLE 9

(R)-α-methyl-3-(trifluoromethyl)benzeneethanamine

The product described in the title having a specific rotatory power $[\alpha]^{25}_D = -20.7°$ (c=1% in ethanol) is obtained from the product described in example 8 working according to the manner described in example 3.

We claim:

1. A process for the production of the isomers (R) or (S)-α-methyl-3-(trifluoromethyl)benzeneethanamine of formula I

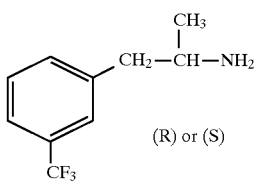

which consists of the following steps:

a) reacting the compound 1-(3-trifluoromethyl)phenyl-2-propanone of formula III

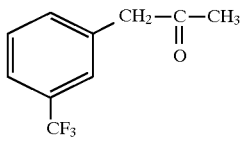

with (R) or (S)-α-methylbenzylamine of formula II

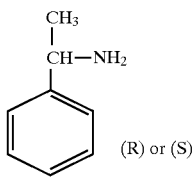

under conditions of a stereospecific reductive amination whereby the diastereoisomer (R),(R) or (S),(S)-N-(1-phenylethyl)-α-methyl-3(trifluoromethyl) benzeneethanamine of formula IV

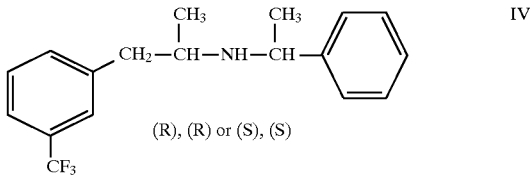

is obtained respectively;

b) debenzylating said compound of formula IV or a salt thereof with an organic or inorganic acid under reducing conditions.

2. The process according to claim 1 wherein said step a) of stereospecific reductive amination is carried out by reacting in a hydrogenator from 1 to 3 molar equivalents of said (R) or (S)-α-methylbenzylamine of formula II and one molar equivalent of said 1-(3-trifluoromethyl)phenyl-2-propanone of formula III in a polar solvent or a mixture of polar and non-polar solvents in the presence of a catalyst and, in the absence or in the presence of an organic or inorganic acid under from 1 to 20 hydrogen atmospheres at a temperature between 20° C. and 100° C. for a period of time between 2 and 24 hours and said step b) of reductive debenzylation is carried out in a hydrogenator in a polar solvent or a mixture of polar and non-polar solvents in the presence of a catalyst under from 1 to 20 hydrogen atmospheres at a temperature between 20° C. and 100° C. for a period of time between 2 and 24 hours.

3. The process according to claim 2 wherein said polar solvent is a member selected from the group consisting of alcohols containing from 1 to 6 carbon atoms, the catalyst of the stereospecific reductive amination in step a) is Raney nickel, the acid in step a) is acetic acid and the catalyst in step b) is palladium on carbon.

4. The process according to claim 2 wherein in step a) said compound III and (S)-α-methylbenzylamine are reacted in equal molar amounts, hydrochloric acid is added at the end of said step a) whereby (S),(S)-N-(1-phenylethyl)-α-methyl-3-(trifluoromethyl)benzeneethanamine hydrochloride is obtained and in step b) the catalyst is palladium on carbon, the solvent is methanol and after completion of the reaction the reaction mixture is made alkaline and said compound I (S)-α-methyl-3-(trifluoromethyl) benzeneethanamine is obtained having $[\alpha]^{25}_D = +20.5°$ (c=1% in ethanol).

* * * * *